US011986353B2

(12) United States Patent
Toh et al.

(10) Patent No.: US 11,986,353 B2
(45) Date of Patent: May 21, 2024

(54) ULTRASONIC DIAGNOSTIC DEVICE, OUTPUT METHOD, AND RECORDING MEDIUM

(71) Applicants: National University Corporation Okayama University, Okayama (JP); CANON MEDICAL SYSTEMS CORPORATION, Tochigi (JP)

(72) Inventors: Norihisa Toh, Okayama (JP); Kousuke Namiki, Otawara (JP); Koichiro Kurita, Nasushiobara (JP)

(73) Assignees: National University Corporation Okayama University, Okayama (JP); CANON MEDICAL SYSTEMS CORPORATION, Tochigi (JP)

( * ) Notice: Subject to any disclaimer, the term of this patent is extended or adjusted under 35 U.S.C. 154(b) by 249 days.

(21) Appl. No.: 17/305,106

(22) Filed: Jun. 30, 2021

(65) Prior Publication Data

US 2021/0401406 A1    Dec. 30, 2021

(30) Foreign Application Priority Data

Jun. 30, 2020 (JP) ................. 2020-112722
Jun. 29, 2021 (JP) ................. 2021-108011

(51) Int. Cl.
*A61B 8/14* (2006.01)
*A61B 8/08* (2006.01)
*A61B 8/00* (2006.01)

(52) U.S. Cl.
CPC ............... *A61B 8/48* (2013.01); *A61B 8/461* (2013.01); *A61B 8/467* (2013.01)

(58) Field of Classification Search
CPC ......... A61B 8/461; A61B 8/463; A61B 8/467; A61B 8/48; A61B 8/5223; A61B 8/5246; A61B 8/54
See application file for complete search history.

(56) References Cited

U.S. PATENT DOCUMENTS 6,454,712 B1   9/2002   Oonuki
2017/0329905 A1*   11/2017   Passerini ................. G06N 5/04

FOREIGN PATENT DOCUMENTS

| JP | 2001-061836 A | 3/2001 |
| JP | 2013-000517 A | 1/2013 |
| JP | 2015-116331 A | 6/2015 |

OTHER PUBLICATIONS

Nagueh et al., "Recommendations for the Evaluation of Left Ventricular Diastolic Function by Echocardiography: An Update from the American Society of Echpcardiography and the European Associatio of Cardiovascular Imaging", Journal of the American Society of Echocardiography, vol. 29, No. 4, Apr. 2006, pp. 277-314.

(Continued)

*Primary Examiner* — Mark D Remaly
(74) *Attorney, Agent, or Firm* — Oblon, McClelland, Maier & Neustadt, L.L.P.

(57) ABSTRACT

An ultrasonic diagnostic device according to an embodiment includes processing circuitry. The processing circuitry estimates a health state on the basis of a measurement value measured using ultrasonic image data. The processing circuitry determines an additional examination used to diagnose the health state, on the basis of the estimated health state. The processing circuitry outputs information indicative of the health state and the additional examination.

10 Claims, 9 Drawing Sheets

(56) References Cited

OTHER PUBLICATIONS

Marwick et al., "Recommendations on the Use of Echocardiography in Adult Hypertension: A Report from the European Association of Cardiovascular Imaging (EACVI) and the American Society of Echocardiography (ASE)", Journal of the American Society of Echocardiography, vol. 28, No. 7, Jul. 2015, pp. 727-754.

Rudski et al., "Guidelines for the Echocardiography Assessment of the Right Heart in Adults: A Report from the American Society of Echocardiography," Journal of the American Society of Echocardiography, Journal of the American Society of Echocardiography, vol. 23, No. 7, Jul. 2010, pp. 685-713.

\* cited by examiner

FIG.4

| SUSPECTED DISEASE | CONDITION FOR MEASUREMENT VALUE |
|---|---|
| LEFT VENTRICULAR DIASTOLIC FAILURE | TWO OR MORE ITEMS OF EF, MV E/e', AND MV e' Vel sep ARE DEVIATING FROM RESPECTIVE NORMAL VALUES |
| RIGHT VENTRICULAR DIASTOLIC FAILURE | ... |
| ⋮ | ⋮ |

FIG.5

| SUSPECTED DISEASE | ADDITIONAL EXAMINATION |
|---|---|
| LEFT VENTRICULAR DIASTOLIC FAILURE | TR VELOCITY, LA VOLUME |
| RIGHT VENTRICULAR DIASTOLIC FAILURE | ... |
| ⋮ | ⋮ |

FIG.6

```
RESULT OF MEASUREMENT
  EF           50.8%
  MV E/e'      12.8       *
  MV e' Vel sep  6.4 cm/s  *

SUSPECTED DISEASE
  LEFT VENTRICULAR
  DIASTOLIC FAILURE

ADDITIONAL EXAMINATION
  1. TR VELOCITY
  2. LA VOLUME
```

FIG.7

```
RESULT OF MEASUREMENT
  EF           50.8%
  MV E/e'      12.8       *
  MV e' Vel sep  6.4 cm/s  *
  TR VELOCITY  3.0 m/s    *

SUSPECTED DISEASE
  LEFT VENTRICULAR
  DIASTOLIC FAILURE

ADDITIONAL EXAMINATION
  1. LA VOLUME
```

FIG.11

|  | AB-SENT | PRE-SENT |
|---|---|---|
| FINDINGS OF CONGENITAL HEART DISEASE | ● | ○ |
| FINDINGS OF VALVULAR DISEASE | ○ | ● |
| FINDINGS OF LEFT VENTRICULAR DILATATION | ● | ○ |
| FINDINGS OF PERICARDIAL DISEASE | ● | ○ |
| FINDINGS OF PULMONARY ARTERIAL HYPERTENSION (PULMONARY HYPERTENSION, SIGNIFICANT DILATATION OF RIGHT VENTRICLE, AND ABSENCE OF DILATATION IN LEFT ATRIUM) | ● | ○ |

[ OK ]  [ CANCEL ]

FIG.12

BNP [　　　　] pg/mL

[ OK ]  [ CANCEL ]

ULTRASONIC DIAGNOSTIC DEVICE, OUTPUT METHOD, AND RECORDING MEDIUM

CROSS-REFERENCE TO RELATED APPLICATIONS

This application is based upon and claims the benefit of priority from Japanese Patent Application No. 2020-112722, filed on Jun. 30, 2020; Japanese Patent Application No. 2021-108011, filed on Jun. 29, 2021; and the entire contents of all of which are incorporated herein by reference.

FIELD

Embodiments disclosed in the present specification and the accompanying drawings relate generally to an ultrasonic diagnostic device, an output method, and an output computer program.

BACKGROUND

An ultrasonic diagnostic device is a device that emits ultrasonic waves generated from piezoelectric transducer elements toward a biological body, receives ultrasonic waves reflected from the inside of the biological body, and images (captures an image of) a state inside the biological body. Since imaging using an ultrasonic diagnostic device comes along with a real-time nature and a non-invasive nature, ultrasonic diagnostic devices have been widely utilized for various types of disease examinations.

In an ultrasonic diagnostic device, a plurality of imaging modes (also referred to as a "scanning mode" and an "imaging mode", for example), in which imaging methods differ from each other, are utilized. There are various types of imaging modes. Example imaging modes include: a B-mode for capturing B-mode image data, an M-mode for capturing M-mode image data, a color Doppler mode for capturing color Doppler image data, a pulse wave (PW) Doppler mode for capturing Doppler waveform data through a PW Doppler method, a continuous wave (CW) Doppler mode for capturing Doppler waveform data through a CW Doppler method, and an elasto mode for capturing a hardness image indicating the hardness of biological tissues through elastography. These imaging modes are each used in accordance with the purpose of an examination.

BRIEF DESCRIPTION OF THE DRAWINGS

FIG. 4 is a view for describing processing that an estimation function according to the embodiment executes;

FIG. 5 is a view for describing processing that a determination function according to the embodiment executes;

FIG. 6 is a view illustrating an example of a display screen according to the embodiment;

FIG. 7 is a view illustrating an example of a display screen after an additional examination is executed, according to the embodiment;

FIG. 11 is a view illustrating an example of an entry screen according to the application example of the embodiment; and FIG. 12 is a view illustrating an example of an entry screen according to the application example of the embodiment.

DETAILED DESCRIPTION

An ultrasonic diagnostic device according to an embodiment includes processing circuitry. The processing circuitry estimates a health state on the basis of a measurement value measured using ultrasonic image data. The processing circuitry determines an additional examination used to diagnose the health state, on the basis of the estimated health state. The processing circuitry outputs information indicative of the health state and the additional examination.

The ultrasonic diagnostic device, an output method, and an output computer program according to the embodiment will now be described with reference to the accompanying drawings. Note that embodiments are not limited to the embodiment described below. Furthermore, it is possible to apply in principle the contents described in one embodiment to other embodiments.

Embodiment

Figure 1:
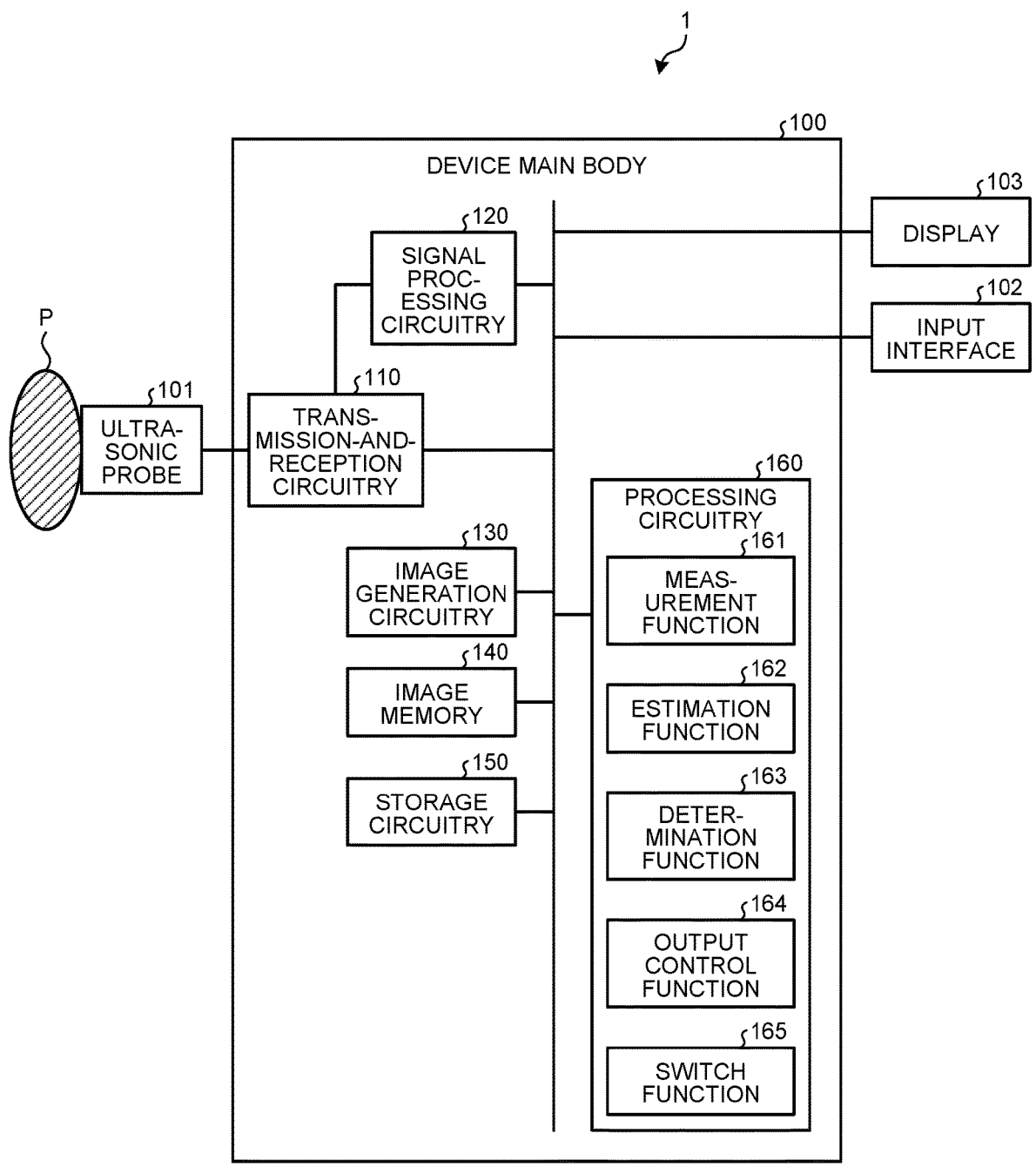
FIG. 1 is a view illustrating a configuration example of an ultrasonic diagnostic device according to an embodiment.

A configuration example of an ultrasonic diagnostic device 1 according to an embodiment will now be described with reference to FIG. 1. FIG. 1 is a view illustrating the configuration example of the ultrasonic diagnostic device 1 according to the embodiment. As illustrated in FIG. 1, the ultrasonic diagnostic device 1 according to the embodiment includes a device main body 100, an ultrasonic probe 101, an input interface 102, and a display 103. The ultrasonic probe 101, the input interface 102, and the display 103 are coupled to the device main body 100. Note that a subject P is not included in the configuration of the ultrasonic diagnostic device 1.

The ultrasonic probe 101 includes a plurality of transducer elements (e.g., piezoelectric transducer elements).

The transducer elements each generate ultrasonic waves on the basis of a drive signal supplied from transmission-and-reception circuitry 110, described later, that the device main body 100 includes. Furthermore, the transducer elements that the ultrasonic probe 101 includes each receive reflective waves from the subject P, and each convert the received reflective waves into electric signals. Furthermore, the ultrasonic probe 101 includes matching layers provided to the transducer elements, and backing materials that prevent ultrasonic waves from propagating rearward from the transducer elements, for example.

When the ultrasonic probe 101 transmits ultrasonic waves into the subject P, the surface, which is discontinuous in acoustic impedance, of a body tissue of the subject P reflects the transmitted ultrasonic waves one after another. The transducer elements that the ultrasonic probe 101 includes receive the reflected, transmitted ultrasonic waves as reflective wave signals (echo signals). The amplitude of a received reflective wave signal depends on a difference in acoustic impedance between the discontinuous surfaces that reflect ultrasonic waves. Note that a reflective wave signal generated when the surface of flowing blood or a cardiac wall, for example, reflects a transmitted ultrasonic pulse is subject to a frequency shift, due to the Doppler effect, depending on a velocity component, in an ultrasonic transmission direction, of a moving body.

Note that it is possible to apply the embodiment to various cases in which the ultrasonic probe 101 illustrated in FIG. 1 is any of a one-dimensional ultrasonic probe in which a plurality of piezoelectric transducer elements are disposed in a line, a one-dimensional ultrasonic probe in which a plurality of piezoelectric transducer elements disposed in a line mechanically oscillate, and a two-dimensional ultrasonic probe in which a plurality of piezoelectric transducer elements are two-dimensionally disposed in a grid.

The input interface 102 includes a mouse, a keyboard, buttons, panel switches, a touch command screen, a foot switch, a trackball, and a joystick, for example. The input interface 102 accepts various types of setting requests from a device operator of the ultrasonic diagnostic device 1, and forwards the accepted various types of setting requests to the device main body 100.

The display 103 displays a graphical user interface (GUI) on which the device operator of the ultrasonic diagnostic device 1, using the input interface 102, enters various types of setting requests. The display 103 also displays ultrasonic image data generated in the device main body 100, for example.

The device main body 100 is a device that generates ultrasonic image data on the basis of a reflective wave signal that the ultrasonic probe 101 receives. As illustrated in FIG. 1, the device main body 100 includes the transmission-and-reception circuitry 110, signal processing circuitry 120, image generation circuitry 130, an image memory 140, storage circuitry 150, and processing circuitry 160. The transmission-and-reception circuitry 110, the signal processing circuitry 120, the image generation circuitry 130, the image memory 140, the storage circuitry 150, and the processing circuitry 160 are communicably coupled to each other.

The transmission-and-reception circuitry 110 controls the ultrasonic probe 101 to execute scanning using ultrasonic waves (ultrasonic scanning). The transmission-and-reception circuitry 110 includes a pulse generator, a transmission delay part, and a pulsar, for example, to supply drive signals to the ultrasonic probe 101. The pulse generator repeatedly generates, at a predetermined rated frequency, rated pulses used to form transmission ultrasonic waves. Furthermore, the transmission delay part causes ultrasonic waves generated from the ultrasonic probe 101 to converge into a beam shape. The transmission delay part further applies, per each of the piezoelectric transducer elements, a delay time that is necessary for determining transmission directional characteristics, to each rated pulse that the pulse generator generates. Furthermore, the pulsar applies a drive signal (a drive pulse) to the ultrasonic probe 101 at a timing based on a rated pulse. That is, the transmission delay part changes a delay time to be applied to each rated pulse to adjust as desired a transmission direction of ultrasonic waves to be transmitted from the surfaces of the piezoelectric transducer elements.

Note that the transmission-and-reception circuitry 110 has a function that is able to instantaneously change a transmission frequency and a transmission drive voltage, for example, in order to execute a predetermined scan sequence on the basis of an instruction that the processing circuitry 160, described later, provides. In particular, changing a transmission drive voltage is achieved with linear amplifier type transmission circuitry that is able to instantly switch a value of the transmission drive voltage, or a mechanism that electrically performs switching among a plurality of power supply units.

Furthermore, the transmission-and-reception circuitry 110 includes a pre-amplifier, an analog/digital (A/D) converter, a reception delay part, and an adder, for example. The transmission-and-reception circuitry 110 executes various types of processing on a reflective wave signal that the ultrasonic probe 101 receives. The transmission-and-reception circuitry 110 then generates reflective wave data. The pre-amplifier amplifies a reflective wave signal per channel. The A/D converter performs an A/D conversion on the amplified reflective wave signal. The reception delay part applies a delay time that is necessary for determining reception directional characteristics. The adder executes addition processing on a reflective wave signal having undergone processing by the reception delay part to generate reflective wave data. As the adder executes the addition processing, a reflective component in a direction in accordance with the reception directional characteristics of a reflective wave signal is emphasized, forming a comprehensive beam when ultrasonic waves are transmitted and received, on the basis of the reception directional characteristics and the transmission directional characteristics.

When a two-dimensional region on the subject P is scanned, the transmission-and-reception circuitry 110 causes the ultrasonic probe 101 to transmit an ultrasonic beam in a two-dimensional direction. The transmission-and-reception circuitry 110 then generates two-dimensional reflective wave data from a reflective wave signal that the ultrasonic probe 101 receives. Furthermore, when a three-dimensional region on the subject P is scanned, the transmission-and-reception circuitry 110 causes the ultrasonic probe 101 to transmit an ultrasonic beam in a three-dimensional direction. The transmission-and-reception circuitry 110 then generates three-dimensional reflective wave data from a reflective wave signal that the ultrasonic probe 101 receives.

The signal processing circuitry 120 executes processing for logarithm amplification and envelope demodulation, for example, on the reflective wave data received from the transmission-and-reception circuitry 110 to generate data (B-mode data) in which signal strength per sampling point is expressed in terms of luminance. The B-mode data that the signal processing circuitry 120 has generated is outputted to the image generation circuitry 130. Note that the B-mode data is an example of scan data.

Furthermore, the signal processing circuitry 120 generates, from the reflective wave data received from the transmission-and-reception circuitry 110, for example, data (Doppler data) acquired by extracting motion information based on the Doppler effect of the moving body at each sampling point within a scan region. Specifically, the signal processing circuitry 120 executes a frequency analysis on velocity information from the reflective wave data, extracts echo components of a blood flow, tissues, and a contrast agent using the Doppler effect, and generates data (Doppler data) acquired by extracting, at a plurality of points, moving body information including average velocity, dispersion, and power, for example. Note herein that a moving body is, for example, a blood flow, a tissue of a cardiac wall, or a contrast agent. The motion information (blood flow information) that the signal processing circuitry 120 has acquired is transmitted to the image generation circuitry 130, and is displayed in color on the display 103 as an average velocity image, a dispersion image, a power image, or an image of a combination thereof. Note that the Doppler data is an example of scan data.

The image generation circuitry 130 generates ultrasonic image data from the data that the signal processing circuitry 120 has generated. The image generation circuitry 130 generates, from the B-mode data that the signal processing circuitry 120 has generated, B-mode image data in which the strength of a reflective wave is expressed in terms of luminance. Furthermore, the image generation circuitry 130 generates, from the Doppler data that the signal processing circuitry 120 has generated, Doppler image data representing the moving body information. The Doppler image data is velocity image data, dispersion image data, power image data, or image data of a combination thereof.

Note herein that the image generation circuitry 130 generally converts (scan-converts) an array of scanning line signals of ultrasonic scanning into an array of scanning line signals conforming to a video format representative of a television format, for example, and generates ultrasonic image data for display purposes. Specifically, the image generation circuitry 130 performs a coordinate-conversion in accordance with a form of ultrasonic scanning that the ultrasonic probe 101 executes, and generates ultrasonic image data for display purposes. Furthermore, the image generation circuitry 130 executes various types of image processing, in addition to the scan conversion, including, for example, image processing (smoothing processing) for re-generating an image having an average luminance value by using a plurality of scan-converted image frames, and image processing (edge enhancement processing) using a differential filter in an image. Furthermore, the image generation circuitry 130 synthesizes ultrasonic image data with supplementary information (e.g., text information of various types of parameters, scales, and body marks).

That is, the B-mode data and the Doppler data are ultrasonic image data that have not yet undergone scan-conversion processing. The data that the image generation circuitry 130 generates is ultrasonic image data for display purposes that has undergone the scan-conversion processing. Note that, when the signal processing circuitry 120 generates three-dimensional scan data (three-dimensional B-mode data and three-dimensional Doppler data), the image generation circuitry 130 performs a coordinate-conversion in accordance with a form of ultrasonic scanning that the ultrasonic probe 101 executes, and generates volume data. The image generation circuitry 130 then executes various types of rendering processing on the volume data to generate two-dimensional image data for display purposes.

The image memory 140 is a memory that stores image data for display purposes (images for display purposes) that the image generation circuitry 130 generates. Furthermore, the image memory 140 is also able to store data that the signal processing circuitry 120 generates. The device operator is able to call, after a diagnosis, for example, the B-mode data and the Doppler data that the image memory 140 has stored. The called data passes through the image generation circuitry 130 to become ultrasonic image data for display purposes.

The storage circuitry 150 stores control programs for executing transmission and reception of ultrasonic waves, image processing, and display processing, diagnosis information (e.g., patient IDs, medical doctors' findings), and various types of data such as diagnosis protocols and various types of body marks. Furthermore, the storage circuitry 150 is used to store, if necessary, image data and other data that the image memory 140 stores. Furthermore, it is possible to forward data that the storage circuitry 150 stores, via a non-illustrated interface, to an external device.

The processing circuitry 160 wholly controls the processing that the ultrasonic diagnostic device 1 executes. Specifically, on the basis of various types of setting requests that the device operator enters via the input interface 102 and various types of control programs and various types of data read from the storage circuitry 150, the processing circuitry 160 controls the processing to be executed in the transmission-and-reception circuitry 110, the signal processing circuitry 120, and the image generation circuitry 130. Furthermore, the processing circuitry 160 controls and causes the display 103 to display ultrasonic image data for display purposes that the image memory 140 stores.

Furthermore, the processing circuitry 160 executes, as illustrated in FIG. 1, a measurement function 161, an estimation function 162, a determination function 163, an output control function 164, and a switch function 165. The measurement function 161 is an example of a measurement unit. The estimation function 162 is an example of an estimation unit. The determination function 163 is an example of a determination unit. The output control function 164 is an example of an output control unit. The switch function 165 is an example of a switch unit.

Note herein that, for example, the processing functions executed by the measurement function 161, the estimation function 162, the determination function 163, the output control function 164, and the switch function 165, which are the components of the processing circuitry 160 illustrated in FIG. 1, each take the form of a computer program executable by a computer, and are recorded in a storage device (e.g., the storage circuitry 150) of the ultrasonic diagnostic device 1. The processing circuitry 160 is a processor that reads, from the storage device, and executes the computer programs to implement the functions corresponding to the computer programs. In other words, the processing circuitry 160 that has read the computer programs possesses the functions illustrated in the processing circuitry 160 in FIG. 1. Note that the processing functions executed by the measurement function 161, the estimation function 162, the determination function 163, the output control function 164, and the switch function 165 will be described later.

The term "processor (circuitry)" used and described above means, for example, a central processing unit (CPU), a graphics processing unit (GPU), or circuitry such as an application specific integrated circuit (ASIC) and a programmable logic device (e.g., a simple programmable logic device (SPLD), a complex programmable logic device (CPLD), and a field programmable gate array (FPGA)). The processor reads and executes the computer programs stored in the storage circuitry 150 to implement the functions. Note that, instead of storing computer programs in the storage circuitry 150, such a configuration may be applied that computer programs are directly incorporated in circuitry in a processor. In this case, the processor reads and executes the computer programs incorporated in the circuitry to implement the functions. The processors according to the present embodiment are not limited to those individually configured as single circuitry. However, a plurality of pieces of independent circuitry may be combined to configure a single processor to implement the functions. Furthermore, the components illustrated in the accompanying drawings may be integrated into a single processor to implement the functions.

By the way, a medical doctor sometimes follows a guideline to perform a diagnosis. For example, when it is suspicious that the circulatory system of a patient is malfunctioning, according to a symptom of and an interview with the patient, the medical doctor first follows a predetermined guideline to evaluate the left ventricular diastolic function. As an example, the volume of the left ventricle, a blood flow velocity at the mitral valve orifice, and a motion velocity of the mitral annular ring, for example, are measured in accordance with the guideline. The medical doctor then performs a diagnosis.

However, the medical doctor has to judge by himself or herself whether each of the measurement values is defined as abnormal in the guideline. Therefore, a medical doctor who neither has much experience nor knowledge may face difficulties in recognizing whether a measurement value corresponds to an abnormal value. As a result, the medical doctor may overlook a disease.

In view of such problems as described above, the ultrasonic diagnostic device 1 according to the present embodiment executes processing described below, in order to reduce overlooked diseases. Note that a case is described below, in which the ultrasonic diagnostic device 1 is utilized to diagnose a disease in the circulatory system. However, utilization cases are not limited to the case described below. It is possible to apply the ultrasonic diagnostic device 1 according to the present embodiment to desired disease diagnoses. Furthermore, the examination items described below are mere examples. It is possible to apply desired examination items.

Figure 2:
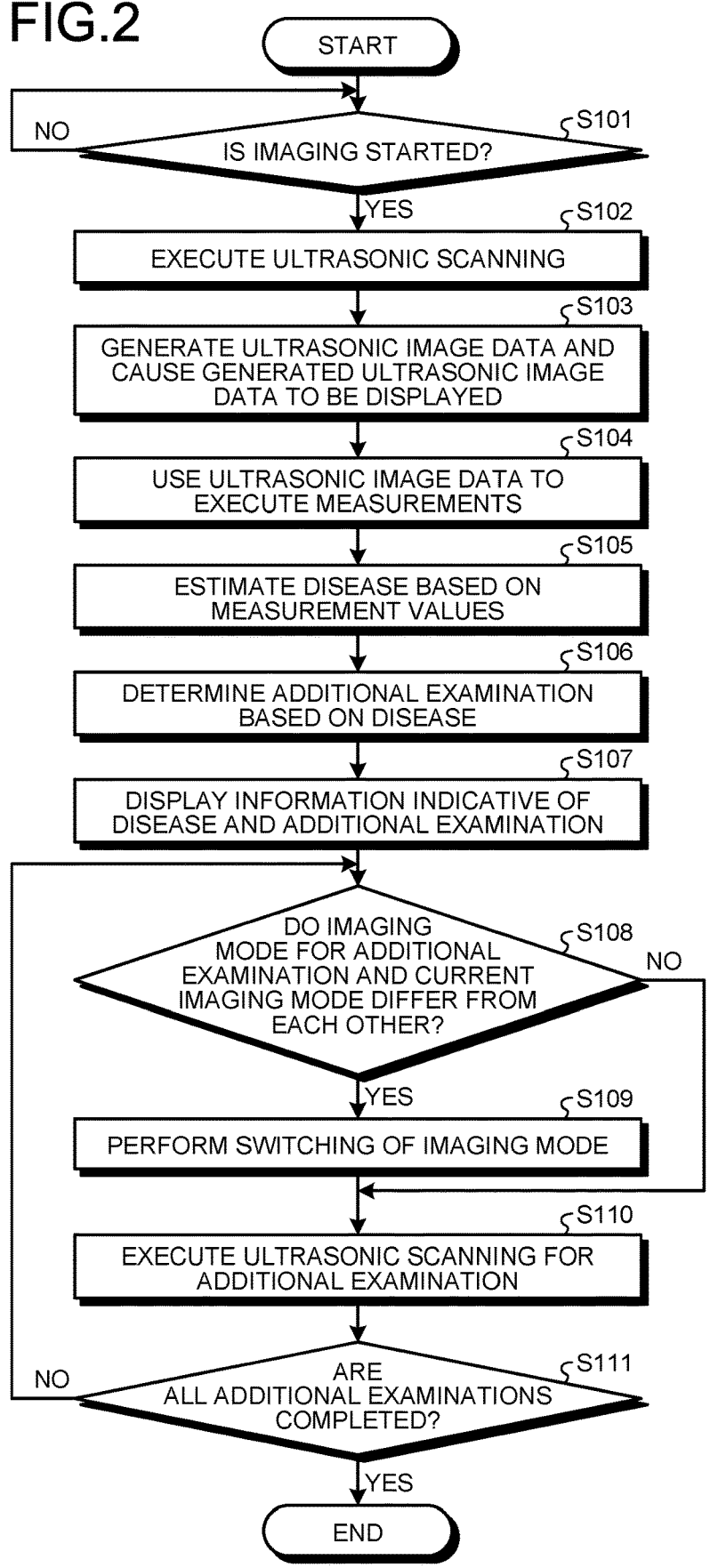
FIG. 2 is a flowchart illustrating a procedure that is to be executed in the ultrasonic diagnostic device according to the embodiment.

A procedure that is to be executed in the ultrasonic diagnostic device 1 according to the embodiment will now be described with reference to FIG. 2. FIG. 2 is a flowchart illustrating the procedure that is to be executed in the ultrasonic diagnostic device 1 according to the embodiment. The description of FIG. 2 proceeds with reference to FIGS. 3 to 7.

The procedure illustrated in FIG. 2 starts when, for example, the device operator enters an instruction of starting imaging (ultrasonic scanning). Note that, as to the procedure illustrated in FIG. 2, its order of steps is not limited to the order of steps illustrated in FIG. 2. The order of steps may be changed as desired within a range where no inconsistency arises in the processing contents.

As illustrated in FIG. 2, when the device operator enters an instruction of starting imaging (positive at step S101), the ultrasonic diagnostic device 1 starts the processing at step S102 and subsequent steps. Note that, before an instruction of starting imaging is entered (negative at step S101), the processing at step S102 and subsequent steps does not start and the processing in FIG. 2 is in a standby state.

When an instruction of starting imaging is entered (positive at step S101), the transmission-and-reception circuitry 110 executes ultrasonic scanning (step S102). For example, the transmission-and-reception circuitry 110 controls the ultrasonic probe 101 to cause the ultrasonic probe 101 to transmit ultrasonic waves into the body of the subject P. Furthermore, the transmission-and-reception circuitry 110 executes various types of processing on reflective wave signals that the ultrasonic probe 101 receives. The transmission-and-reception circuitry 110 then generates reflective wave data. The signal processing circuitry 120 then generates scan data from the reflective wave data that the transmission-and-reception circuitry 110 has generated.

Next, the image generation circuitry 130 generates ultrasonic image data and causes the generated ultrasonic image data to be displayed (step S103). For example, the image generation circuitry 130 generates the ultrasonic image data from the scan data that the signal processing circuitry 120 has generated. The processing circuitry 160 (the output control function 164) then causes the display 103 to display the generated ultrasonic image data.

Figure 3:
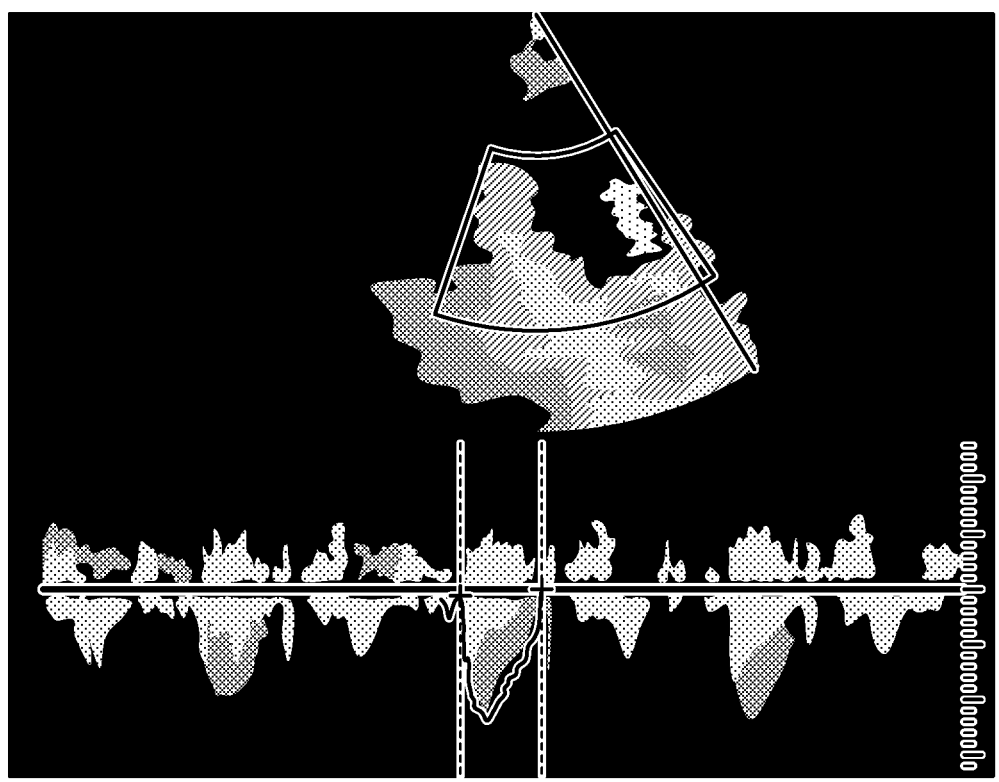
FIG. 3 is a view illustrating a display example of ultrasonic image data according to the embodiment.

A display example of the ultrasonic image data according to the embodiment will now be described with reference to FIG. 3. FIG. 3 is a view illustrating the display example of the ultrasonic image data according to the embodiment. The upper side of FIG. 3 illustrates B-mode image data. The lower side of FIG. 3 illustrates velocity image data.

As illustrated in FIG. 3, for example, the output control function 164 causes the display 103 to display the B-mode image data and the velocity image data. On the B-mode image data, measurement calipers are illustrated to indicate a position at which a blood flow velocity is measured. The velocity image data indicates time series variations of the blood flow velocity measured under the CW Doppler mode at the measurement position that the measurement calipers indicate.

The measurement function 161 then uses the ultrasonic image data to execute measurements (step S104). For example, the measurement function 161 performs measurements for a plurality of measurement items on the basis of the ultrasonic image data, and acquires measurement values.

As an example, the measurement function 161 performs measurements for three measurement items of "EF", "MV E/e'", and "MV e' Vel sep". Note herein that the term "EF" represents an ejection fraction (EF) in the left ventricle. Furthermore, the term "MV E/e'" represents a ratio between an early diastolic wave (E) in a waveform of a blood flow velocity at the mitral valve orifice and an early diastolic wave (e') in a waveform of a motion velocity of the mitral annular ring. Furthermore, the term "MV e' Vel sep" represents a motion velocity on the septum side (Sep) of the mitral annular ring.

Note that the types of measurement items are not limited to "EF", "MV E/e'", and "MV e' Vel sep". It is possible to set desired measurement items. Furthermore, for methods of measuring measurement items, it is possible to apply desired known technologies.

The estimation function 162 then estimates a disease on the basis of the measurement values (step S105). For example, the estimation function 162 refers to information (a disease estimation table) in which diseases and conditions for measurement values are respectively associated with each other, and estimates a disease on the basis of the measurement values that the measurement function 161 measures.

The processing that the estimation function 162 according to the embodiment executes will now be described with reference to FIG. 4. FIG. 4 is a view for describing the processing that the estimation function 162 according to the embodiment executes. FIG. 4 illustrates the disease estimation table to which the estimation function 162 refers. Note that the disease estimation table is stored beforehand in the storage circuitry 150, for example.

As illustrated in FIG. 4, in the disease estimation table, a suspected disease "Left ventricular diastolic failure" and a condition for measurement value "Two or more items of EF, MV E/e', and MV e' Vel sep are deviating from respective normal values" are associated with each other. The association indicates that a suspected disease is left ventricular diastolic failure, when two or more items of "EF", "MV E/e'", and "MV e' Vel sep" are deviating from respective normal values. Note that, although FIG. 4 illustrates the example of left ventricular diastolic failure, other diseases are similarly stored.

For example, the estimation function 162 cross-checks the measurement values that the measurement function 161 has measured with the conditions described under the title "Condition for measurement value" in the disease estimation table. Specifically, a threshold value is used for a determination of whether a measurement value corresponds to a normal value or an abnormal value. For example, a normal value for "EF" corresponds to a value equal to or above 50 [%]. An abnormal value corresponds to a value below 50 [%]. Furthermore, a normal value for "MV E/e'" corresponds to a value below 14. An abnormal value corresponds to a value equal to or above 14. Furthermore, a normal value for "MV e' Vel sep" corresponds to a value equal to or above 7 [cm/s]. An abnormal value corresponds to a value below 7 [cm/s].

Note herein that, for example, a case in which a value of "EF" corresponds to the normal value, and values of "MV E/e'" and "MV e' Vel sep" respectively correspond to the abnormal values meets the condition "Two or more items of EF, MV E/e', and MV e' Vel sep are deviating from respective normal values". In this case, the estimation function 162 estimates that the subject P is suffering from "Left ventricular diastolic failure".

Note that the processing that the estimation function 162 executes, described above, is a mere example. Embodiments are not limited to the processing described above. For example, it is possible to set processing that the estimation function 162 executes as desired in accordance with a guideline. Furthermore, the processing of estimating a disease is not limited to such processing using a threshold value. It is possible to apply, to the processing of estimating a disease, for example, a learned model constructed to estimate a disease.

Furthermore, a disease (a disease name) that the estimation function 162 estimates is to help the medical doctor perform a diagnosis, but is not to make a definite diagnosis. The medical doctor is still responsible for the final diagnosis.

The determination function 163 then determines an additional examination on the basis of the estimated disease (step S106). For example, the determination function 163 refers to information (an additional examination table) in which diseases and additional examinations are associated with each other, and determines an additional examination corresponding to the disease that the estimation function 162 has estimated.

The processing that the determination function 163 according to the embodiment executes will now be described with reference to FIG. 5. FIG. 5 is a view for describing the processing that the determination function 163 according to the embodiment executes. FIG. 5 illustrates the additional examination table to which the determination function 163 refers. Note that the additional examination table is stored beforehand in the storage circuitry 150, for example.

As illustrated in FIG. 5, in the additional examination table, a suspected disease "Left ventricular diastolic failure" and additional examinations "TR Velocity, LA Volume" are associated with each other. The association indicates that two examination items of "TR Velocity" and "LA Volume" are determined as additional examinations when a suspected disease is left ventricular diastolic failure. Note that, although FIG. 5 illustrates the example of left ventricular diastolic failure, other diseases are similarly stored.

For example, the determination function 163 refers to the additional examination table, and determines an additional examination corresponding to the disease that the estimation function 162 has estimated. In the example in FIG. 5, the determination function 163 determines two examination items of "TR Velocity" and "LA Volume" as additional examinations to "Left ventricular diastolic failure".

Note herein that the determination function 163 determines an additional examination on the basis of a current imaging mode used to capture the ultrasonic image data. For example, the determination function 163 determines, when there are a plurality of candidate additional examinations, a degree of priority for each of the candidate additional examinations.

As an example, the determination function 163 determines a degree of priority for each of the candidate additional examinations on the basis of whether the each of the additional examinations is an additional examination that is to be executed under an imaging mode identical to the current imaging mode. Note that the determined additional examination "TR Velocity" in FIG. 5 is measured under the CW Doppler mode, and "LA Volume" is measured under the B-mode.

Note herein that, when the current imaging mode is the CW Doppler mode, the determination function 163 determines that a degree of priority for "TR Velocity" measured under the identical imaging mode is high, and determines that a degree of priority for "LA Volume" measured under a different imaging mode is low. As a result, a priority order for "TR Velocity" is set to "1", and a priority order for "LA Volume" is set to "2". Note that, as to the priority order, when the value is smaller, its degree of priority is higher.

Note that the processing that the determination function 163 executes, described above, is a mere example. Embodiments are not limited to the processing described above. For example, the case has been described above, in which whether a degree of priority is high or low is indicated as a priority order. However, embodiments are not limited to the case described above. For example, a degree of priority may be defined to be high, when the value is larger.

The output control function 164 then causes information indicative of the disease and the additional examination to be displayed (step S107). For example, the output control function 164 causes the display 103 to display information indicative of the degrees of priority for the candidate additional examinations and the additional examinations.

An example of a display screen according to the embodiment will now be described with reference to FIG. 6. FIG. 6 is a view illustrating the example of the display screen according to the embodiment. FIG. 6 illustrates a window including "Result of measurement", "Suspected disease", and "Additional examination".

As illustrated in FIG. 6, the output control function 164 causes the display 103 to display the window including "Result of measurement", "Suspected disease", and "Additional examination". Note herein that "Result of measurement" includes the measurement items measured through the processing executed so far, the measurement values, and information indicating that the measurement values are abnormal.

For example, the output control function 164 causes the three measurement items of "EF", "MV E/e'", and "MV e' Vel sep" that the measurement function 161 has measured to be displayed as "Result of measurement". In the example in FIG. 6, "EF" is 50.8 [%], "MV E/e'" is 12.8, and "MV e' Vel sep" is 6.4 [cm/s]. Furthermore, the output control function 164 causes "*" to be displayed as information indicative of the fact that the measurement value is abnormal. In the example in FIG. 6, the output control function 164 causes "*" to be displayed on the right side of each of "MV E/e'" and "MV e' Vel sep". The mark indicates that the values of "MV E/e'" and "MV e' Vel sep" are abnormal.

Note that, for convenience of illustration, the case has been described above, in which "*" is displayed as the fact that the measurement value is abnormal. However, embodiments are not limited to the case described above. For example, a measurement value may be indicated in a color (e.g., red) that differs from the color of other characters. A measurement value may be displayed in an underlined manner. A measurement value may be displayed in a frame-surrounded manner.

Furthermore, the output control function 164 causes the text "Left ventricular diastolic failure" that the estimation function 162 has estimated to be displayed as "Suspected disease". Note that, when the estimation function 162 estimates that there are a plurality of suspected diseases, the diseases may be displayed.

Furthermore, the output control function 164 causes additional examinations that the determination function 163 has determined to be displayed as "Additional examination", together with the degrees of priority. As an example, the output control function 164 causes "1. TR Velocity" and "2. LA Volume" to be displayed in the priority order.

Note that the processing that the output control function 164 executes, described above, is a mere example. Embodiments are not limited to the processing described above. For example, the form of output from the output control function 164 is not limited to displaying. For example, means such as a voice or a vibration pattern may be outputted. Furthermore, the output control function 164 may transmit information to be outputted to an external device (another desired device than the ultrasonic diagnostic device 1). The external device that is the transmission destination may then output the information in a desired output form.

The switch function 165 then determines whether an imaging mode for an additional examination and the current imaging mode differ from each other (step S108). At this time, when there are a plurality of additional examinations, the switch function 165 determines whether the imaging mode for one of the additional examinations that has the highest degree of priority and the current imaging mode differ from each other.

Note herein that when it is determined that the imaging mode for the additional examination and the current imaging mode differ from each other (positive at step S108), the switch function 165 performs switching of the imaging mode (step S109). For example, when the imaging mode for the additional examination is the "B-mode", and the current imaging mode is the "CW Doppler mode", the switch function 165 performs switching of the imaging mode from the "CW Doppler mode" to the "B-mode". On the other hand, when it is not determined that the imaging mode for the additional examination and the current imaging mode differ from each other (negative at step S108), the switch function 165 does not execute the processing at step S109, but causes the procedure to proceed to the processing at step S110.

The transmission-and-reception circuitry 110 then executes ultrasonic scanning for the additional examination (step S110). The image generation circuitry 130 then generates ultrasonic image data for the additional examination, and causes the generated ultrasonic image data to be displayed. Furthermore, the measurement function 161 uses the ultrasonic image data for the additional examination to execute measurements. Upon the execution of the measurements for the additional examination, the output control function 164 updates the display screen.

An example of a display screen after an additional examination is executed, according to the embodiment, will now be described with reference to FIG. 7. FIG. 7 is a view illustrating the example of the display screen after the additional examination is executed, according to the embodiment. The display screen illustrated in FIG. 7 is an updated display screen from the display screen illustrated in FIG. 6, upon the execution of the additional examination "TR Velocity".

As illustrated in FIG. 7, the output control function 164 adds a measurement value acquired through the additional examination "TR Velocity" into the field of "Result of measurement". In the example illustrated in FIG. 7, the measurement value of "TR Velocity" is 3.0 [m/s]. Furthermore, the output control function 164 causes "*" to be displayed as information indicative of the fact that the measurement value is abnormal. Note that "TR Velocity" is determined to be abnormal when its value is equal to or above 2.8 [m/s].

Furthermore, the output control function 164 deletes the item "TR Velocity" from the items of "Additional examination", upon the execution of the additional examination "TR Velocity". The output control function 164 then moves up the priority orders of the remaining additional examinations. As a result, the output control function 164 causes "1. LA Volume" to be displayed as "Additional examination" in FIG. 7.

The processing circuitry 160 then determines whether all additional examinations are completed (step S111). When there is an additional examination left (negative at step S111), the processing circuitry 160 causes the procedure to proceed to the processing at step S108. When all the additional examinations are completed (positive at step S111), the processing circuitry 160 ends the procedure in FIG. 2.

As described above, in the ultrasonic diagnostic device 1 according to the embodiment, the estimation function 162 estimates a disease on the basis of a measurement value measured using ultrasonic image data. The determination function 163 determines an additional examination used to diagnose a disease, on the basis of the estimated disease. The output control function 164 outputs information indicative of the disease and the additional examination. Therefore, with the ultrasonic diagnostic device 1, it is possible to reduce overlooked diseases. For example, even a medical doctor who neither has much experience nor knowledge is able to refer to diseases and additional examinations that the ultrasonic diagnostic device 1 presents to reduce overlooked diseases.

Furthermore, for example, the ultrasonic diagnostic device 1 determines an additional examination on the basis of the current imaging mode. For example, the ultrasonic diagnostic device 1 presents, on a priority basis, an imaging mode identical to the current imaging mode when there are a plurality of candidate additional examinations. Therefore, the ultrasonic diagnostic device 1 is able to keep a minimum number of times of switching of the imaging mode even when there are a plurality of additional examinations, making it possible to smoothly execute a series of examinations.

Furthermore, for example, the ultrasonic diagnostic device 1 automatically performs switching of the imaging mode when the imaging mode for an additional examination and the current imaging mode differ from each other. Therefore, the ultrasonic diagnostic device 1 is able to reduce efforts of switching by a device operator (a medical doctor).

Conventionally, in an ultrasonic diagnostic device, various types of imaging modes are each used in accordance with the purpose of an examination. However, as imaging modes increase in type, a device operator is required to have much experience and knowledge in order to fully use the imaging modes. The ultrasonic diagnostic device 1 according to the embodiment can smoothly execute necessary additional examinations while appropriately presenting them. Therefore, it is possible to utilize the strength of incorporating various types of imaging modes, without relying on the experience and knowledge of a device operator.

Application Example

An application example of the embodiment described above will now be described. Note herein that a case when the ultrasonic diagnostic device 1 according to the embodiment described above is applied to a diagnosis for heart failure will be described.

Figure 8:
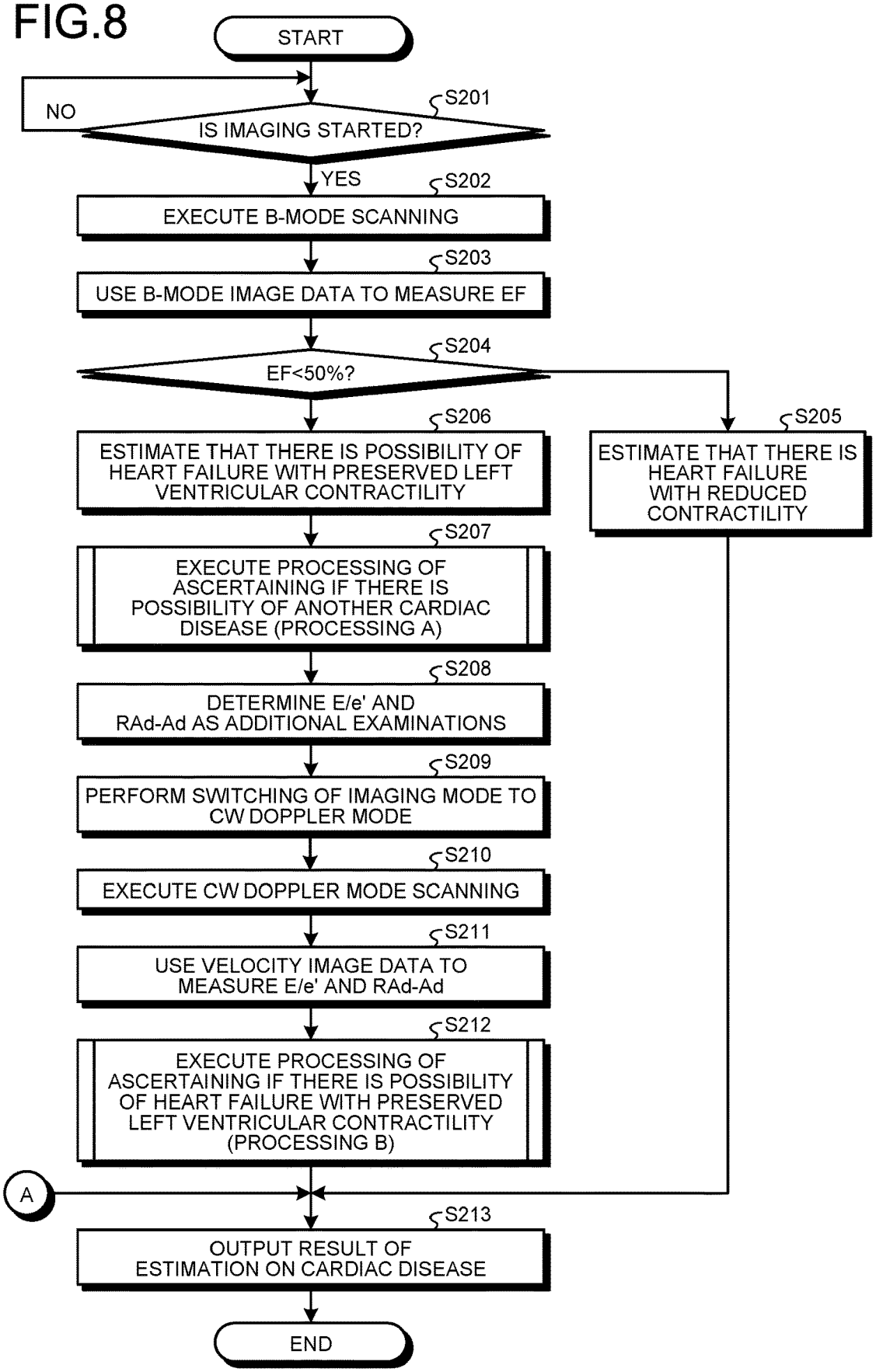
FIG. 8 is a flowchart illustrating a procedure that is to be executed in the ultrasonic diagnostic device according to an application example of the embodiment.
Figure 9:
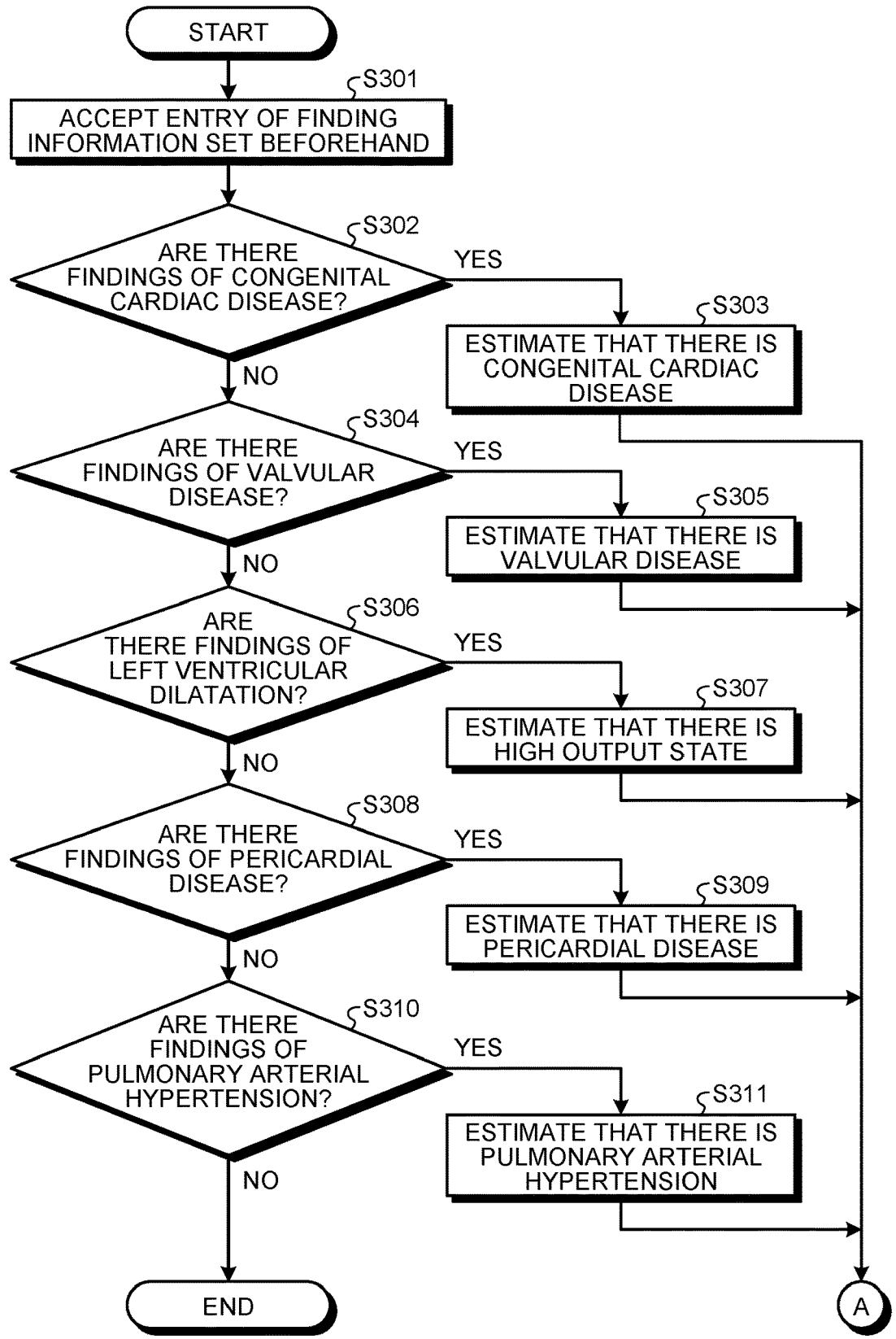
FIG. 9 is a flowchart illustrating a procedure that is to be executed in the ultrasonic diagnostic device according to the application example of the embodiment.
Figure 10:
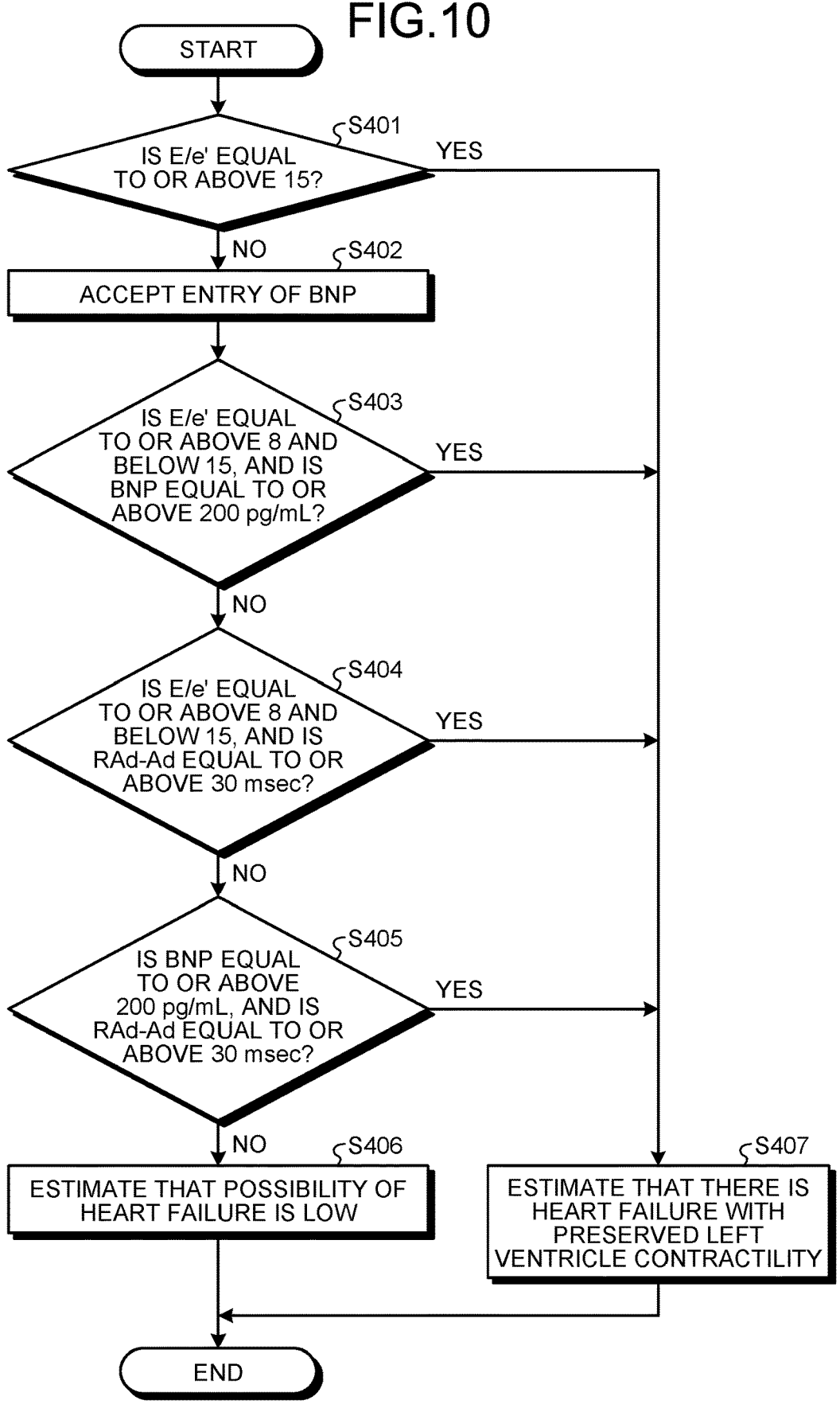
FIG. 10 is a flowchart illustrating a procedure that is to be executed in the ultrasonic diagnostic device according to the application example of the embodiment.

FIGS. 8, 9, and 10 are flowcharts illustrating procedures that are to be executed in the ultrasonic diagnostic device according to the application example of the embodiment. Note that FIG. 9 is the flowchart illustrating a detailed procedure in the processing at step S207 in FIG. 8. Furthermore, FIG. 10 is the flowchart illustrating a detailed procedure in the processing at step S212 in FIG. 8. Furthermore, the description of FIGS. 8 to 10 proceeds with reference to FIGS. 11 and 12. FIGS. 11 and 12 are views each illustrating an example of an entry screen according to the application example of the embodiment.

The procedure illustrated in FIG. 8 starts when, for example, the device operator enters an instruction of starting imaging (ultrasonic scanning).

As illustrated in FIG. 8, when the device operator enters an instruction of starting imaging (positive at step S201), the ultrasonic diagnostic device 1 starts the processing at step S202 and subsequent steps. Note that, before an instruction of starting imaging is entered (negative at step S201), the processing at step S202 and subsequent steps does not start. That is, the procedure in FIG. 8 is in a standby state.

When an instruction of starting imaging is entered (positive at step S201), the transmission-and-reception circuitry 110 executes B-mode scanning (step S202). The image generation circuitry 130 then generates B-mode image data and causes the generated B-mode image data to be displayed. Note that the processing at step S202 corresponds to the processing at steps S102 and S103 in FIG. 2.

Next, the measurement function 161 uses the B-mode image data to measure EF (step S203). Note herein that the term "EF" represents an ejection fraction in the left ventricle, as described above, and is measured on the basis of a change in volume in the left ventricle calculated from the B-mode image data. Note that the processing at step S203 corresponds to the processing at step S104 in FIG. 2.

The estimation function 162 then determines whether EF is below 50 (step S204). Note herein that, when EF is below 50 (positive at step S204), the estimation function 162 estimates that there is heart failure with reduced contractility (step S205), and causes the procedure to proceed to the processing at step S213. On the other hand, when EF is equal to or above 50 (negative at step S204), the estimation function 162 estimates that there is a possibility of heart failure with preserved left ventricular contractility (step S206), and causes the procedure to proceed to the processing at step S207.

Note that a disease that the estimation function 162 estimates may not be necessarily a certain "disease name". For example, as illustrated in FIG. 8, it is possible that the estimation function 162 estimates a "health state" such as "heart failure with reduced contractility" or "there is a possibility of heart failure with preserved left ventricular contractility". The estimation processing described above is achieved with tables set beforehand, predetermined mathematical functions, and processing with threshold values, for example.

The estimation function 162 then executes the processing of ascertaining if there is a possibility of another cardiac disease (processing A) (step S207). The procedure of the processing A will now be described with reference to FIG. 9. Note that the mark "A" in FIG. 9 is linked to the mark "A" in FIG. 8, indicating that the procedure proceeds to step S213.

As illustrated in FIG. 9, the estimation function 162 accepts finding information set beforehand (step S301). For example, the estimation function 162 causes the display 103 to display the entry screen illustrated in FIG. 11, and, using the entry screen, accepts the finding information set beforehand. Note that the finding information is an example of "non-image information" that differs from the ultrasonic image data.

In the example illustrated in FIG. 11, the entry screen displays various types of findings and radio buttons used to enter whether each of the findings are present or absent, in association with each other. Specifically, the entry screen displays findings of congenital cardiac disease, findings of valvular disease, findings of left ventricular dilatation, findings of pericardial disease, and findings of pulmonary arterial hypertension, and the radio buttons used to enter whether the findings are present or absent. For example, the device operator (the medical doctor) refers to the entry screen illustrated in FIG. 11. When there are findings regarding the subject P, the device operator (the medical doctor) selects the radio button that indicates that there are the corresponding findings, and then presses the OK button. As a result, the estimation function 162 accepts the finding information indicative of whether there are various types of findings regarding the subject P. Note that findings of pulmonary arterial hypertension are judged on the basis of the fact that there is pulmonary hypertension, significant dilatation of the right ventricle, and absence of dilatation in the left atrium.

Next, the estimation function 162 determines whether there are findings of congenital cardiac disease (step S302). Note herein that, when there are findings of congenital cardiac disease (positive at step S302), the estimation function 162 estimates that there is congenital cardiac disease (step S303), and causes the procedure to proceed to the processing at step S213.

On the other hand, when there is no finding of congenital cardiac disease (negative at step S302), the estimation function 162 determines whether there are findings of valvular disease (step S304). Note herein that, when there are findings of valvular disease (positive at step S304), the estimation function 162 estimates that there is valvular disease (step S305), and causes the procedure to proceed to the processing at step S213.

On the other hand, when there is no finding of valvular disease (negative at step S304), the estimation function 162 determines whether there are findings of left ventricular dilatation (step S306). Note herein that, when there are findings of left ventricular dilatation (positive at step S306), the estimation function 162 estimates that there is high output state (step S307), and causes the procedure to proceed to the processing at step S213.

On the other hand, when there is no finding of left ventricular dilatation (negative at step S306), the estimation function 162 determines whether there are findings of pericardial disease (step S308). Note herein that, when there are findings of pericardial disease (positive at step S308), the estimation function 162 estimates that there is pericardial disease (step S309), and causes the procedure to proceed to the processing at step S213.

On the other hand, when there is no finding of pericardial disease (negative at step S308), the estimation function 162 determines whether there are findings of pulmonary arterial hypertension (step S310). Note herein that, when there are findings of pulmonary arterial hypertension (positive at step S310), the estimation function 162 estimates that there is pulmonary arterial hypertension (step S311), and causes the procedure to proceed to the processing at step S213.

On the other hand, when there is no finding of pulmonary arterial hypertension (negative at step S310), the estimation function 162 ends the processing A illustrated in FIG. 9, and causes the procedure to proceed to the processing at step S208 in FIG. 8. Note that the processing from steps S204 to S207 corresponds to the processing at step S105 in FIG. 2.

That is, as illustrated in FIG. 9, the estimation function 162 estimates the health state on the basis of the non-image information.

Now the description goes back to FIG. 8. The determination function 163 then determines E/e' and RAd-Ad as additional examinations (step S208). For example, since it is considered that there is a possibility of heart failure with preserved left ventricular contractility and a low possibility of another cardiac disease, the determination function 163 determines E/e' and RAd-Ad as additional examinations.

Note herein that "E/e'" is similar to "MV E/e'" described above. Furthermore, the term "RAd-Ad" represents a difference between a width of an atrial systolic wave in a waveform of a blood flow velocity in a pulmonary vein (RAd) and a width of an atrial systolic wave in a waveform of a blood flow velocity into the left ventricle (Ad). It is possible to measure both E/e' and RAd-Ad on the basis of velocity image data (data collected under the CW Doppler mode). Note that the processing at step S208 corresponds to the processing at step S106 in FIG. 2.

The switch function 165 then performs switching of the imaging mode to the CW Doppler mode (step S209). For example, because the imaging mode capable of measuring both E/e' and RAd-Ad is the "CW Doppler mode", which differs from the imaging mode (the current imaging mode), that is, the "B-mode", used at step S202, the switch function 165 performs switching of the imaging mode to the CW Doppler mode. Note that the processing at step S209 corresponds to the processing at steps S108 and S109 in FIG. 2.

The transmission-and-reception circuitry 110 then executes CW Doppler mode scanning (step S210). The image generation circuitry 130 then generates velocity image data on the basis of data collected through the CW Doppler mode scanning and causes the generated velocity image data to be displayed. Note that the processing at step S210 corresponds to the processing at step S111 in FIG. 2.

The measurement function 161 then uses the velocity image data to measure E/e' and RAd-Ad (step S211). For methods of measuring E/e' and RAd-Ad, it is possible to apply desired known technologies.

The estimation function 162 then executes the processing of ascertaining if there is a possibility of heart failure with preserved left ventricular contractility (processing B) (step S212). The procedure of the processing B will now be described with reference to FIG. 10.

As illustrated in FIG. 10, the estimation function 162 determines whether E/e' is equal to or above 15 (step S401). When E/e' is equal to or above 15 (positive at step S401), the estimation function 162 estimates that there is heart failure with preserved left ventricular contractility (step S407), and then ends the processing B.

On the other hand, when E/e' is below 15 (negative at step S401), the estimation function 162 accepts the entry of BNP (step S402). Note herein that the term "BNP" represents the amount of brain (B-type) natriuretic peptide in blood, and is measured through a blood examination (or a BNP examination). For example, the estimation function 162 causes the display 103 to display the entry screen illustrated in FIG. 12, and, using the entry screen, accepts the entry of BNP.

In the example illustrated in FIG. 12, the entry screen displays an entry field used to accept the entry of a numerical value of BNP. For example, the device operator (the medical doctor) enters, in the entry field illustrated in FIG. 12, a value of BNP of the subject P, which is measured through the blood examination performed beforehand. The device operator (the medical doctor) then presses the OK button. As a result, the estimation function 162 accepts the entered value of BNP of the subject P. Note that BNP is an example of "non-image information".

The estimation function 162 then determines whether E/e' is equal to or above 8 and below 15, and BNP is equal to or above 200 pg/mL (step S403). When E/e' is equal to or above 8 and below 15, and BNP is equal to or above 200 pg/mL (positive at step S403), the estimation function 162 estimates that there is heart failure with preserved left ventricular contractility (step S407), and then ends the processing B.

On the other hand, when it is not determined that E/e' is equal to or above 8 and below 15, and BNP is equal to or above 200 pg/mL (negative at step S403), the estimation function 162 determines whether E/e' is equal to or above 8 and below 15, and RAd-Ad is equal to or above 30 msec (step S404). When E/e' is equal to or above 8 and below 15, and RAd-Ad is equal to or above 30 msec (positive at step S404), the estimation function 162 estimates that there is heart failure with preserved left ventricular contractility (step S407), and then ends the processing B.

On the other hand, when it is not determined that E/e' is equal to or above 8 and below 15, and RAd-Ad is equal to or above 30 msec (negative at step S404), the estimation function 162 determines whether BNP is equal to or above 200 pg/mL, and RAd-Ad is equal to or above 30 msec (step S405).

When BNP is equal to or above 200 pg/mL, and RAd-Ad is equal to or above 30 msec (positive at step S405), the estimation function 162 estimates that there is heart failure with preserved left ventricular contractility (step S407), and then ends the processing B.

On the other hand, when it is not determined that BNP is equal to or above 200 pg/mL, and RAd-Ad is equal to or above 30 msec (negative at step S405), the estimation function 162 estimates that a possibility of heart failure is low (step S406), and then ends the processing B.

That is, as illustrated in FIG. 10, the estimation function 162 estimates the health state on the basis of the non-image information.

Now the description goes back to FIG. 8. The output control function 164 outputs the result of the estimation on cardiac disease (step S213). For example, the output control function 164 causes the display 103 to display the result of estimation that the estimation function 162 has estimated. The ultrasonic diagnostic device 1 then ends the procedure in FIG. 8.

Note that the procedures illustrated in FIGS. 8 to 10 are mere examples. Embodiments are not limited to the examples described above. For example, it is possible to appropriately change the order of steps in the processing illustrated in FIGS. 8 to 10 within a range where no inconsistency arises in processing contents. For example, the processing of accepting the entry of finding information (step S301) and the processing of accepting the entry of BNP (step S402) may be executed at an earlier stage.

Furthermore, in FIGS. 8 to 10, as to the processing of accepting the entry of finding information (step S301) and the processing of accepting the entry of BNP (step S402), the case has been described above, in which the entry is achieved through a manual operation by the device operator. However, embodiments are not limited to the case described above. For example, when finding information and BNP were examined, the finding information and the BNP may be automatically acquired from the examination results. For example, when reservation information for an ultrasonic cardiac disease examination for a subject P is transmitted from an examination reservation system to the ultrasonic diagnostic device 1, finding information and the value of BNP may also be transmitted from the examination reservation system to the ultrasonic diagnostic device 1, if the finding information and the value of BNP have been examined.

Furthermore, in the example described above, the case in which "BNP" is used has been described. However, "NT-proBNP" may be used. Note that "NT-proBNP" is a hormone that is generated when proBNP that is a precursor hormone is decomposed, and that is discharged into blood together with BNP in a ratio of 1:1. The value of "NT-proBNP" serves as an index value used to aid a heart failure diagnosis, similarly to BNP.

Furthermore, in the example described above, the case in which "RAd-Ad" is used has been described. However, at least one of "left atrial volume index", "left atrial dimension", "left ventricular mass index", and "findings of atrial fibrillation" may be used. It is possible to measure the "left atrial volume index", the "left atrial dimension", and the "left ventricular mass index" on the basis of B-mode image data of the left ventricle. Furthermore, the "findings of atrial fibrillation" are information judged through an electrocardiogram examination. It is possible to acquire the "findings of atrial fibrillation" through a manual operation by a device operator or to automatically acquire from an examination reservation system, for example.

Modification Examples

In the embodiment described above, the case has been described above, in which a degree of priority for an additional examination is determined on the basis of whether the imaging mode is identical to the current imaging mode. However, embodiments are not limited to the case described above. For example, a degree of priority may be determined on the basis of whether each of the additional examinations is to be executed under the B-mode.

Since the B-mode image data is acquired by imaging a tomographic view of the inside of a biological body, the B-mode is an optimum imaging mode allowing a device operator to know the situation inside the body of a subject P. Furthermore, the B-mode image data is also utilized as a background image for another imaging mode to specify positions of a region of interest, measurement calipers, and annotations, for example. Due to the reasons described above, it can be said that the B-mode is one of major imaging modes used in an ultrasonic diagnostic device.

In view of the reasons described above, the determination function 163 may determine a degree of priority for each of candidate additional examinations on the basis of whether each of the additional examinations is to be executed under the "B-mode". For example, when there are, as a plurality of candidate additional examinations, an additional examination that is to be executed under the "B-mode" and an additional examination that is to be executed under another imaging mode, the determination function 163 determines that the degree of priority for the additional examination that is to be executed under the "B-mode" is higher than the degree of priority for the additional examination that is to be executed under the other imaging mode.

Note that, when there are, as a plurality of candidate additional examinations, additional examinations that are to be executed under "an imaging mode identical to the current imaging mode" and the "B-mode", it is preferable that the additional examination that is to be executed under "the imaging mode identical to the current imaging mode" is prioritized. That is, the determination function 163 determines that the degree of priority for the additional examination that is to be executed under the "B-mode" is high, when there is no additional examination that is to be executed under the imaging mode identical to the current imaging mode, among the candidate additional examinations. However, when the initial imaging mode is not the B-mode, the determination function 163 may determine that the degree of priority for the additional examination that is to be executed under the "B-mode" is higher than the degree of priority for the additional examination that is to be executed under "the imaging mode identical to the current imaging mode".

Other Embodiments

Embodiments may be implemented in other various types of forms, other than the form used in the embodiment described above.

Furthermore, the components of the devices are functionally and conceptually illustrated, and are not necessarily physically configured as illustrated. That is, a specific form of distribution or integration of the devices is not limited to the forms illustrated in the drawings. The devices may be wholly or partially and functionally or physically configured in a dispersed or integrated manner in terms of a desired unit in accordance with various kinds of loads and use situations, for example. Furthermore, the processing functions implemented in the devices may be wholly or partially implemented as desired by a CPU and a computer program analyzed and executed by the CPU, or implemented by hardware using wired logic.

Furthermore, among the steps of the processing described in the foregoing embodiments, it is possible to execute manually some or all of the steps of the processing that has been described to be executed automatically. Otherwise, it is possible to execute automatically, with a known method, some or all of the steps of the processing that has been described to be executed manually. In addition, unless otherwise specifically described, it is possible to alter as desired the procedure, the control procedure, the specific names, and information including various types of data and parameters described above in the specification and the accompanying drawings.

Furthermore, the output method (the ultrasonic imaging method) described in the foregoing embodiment can be implemented by causing a computer, such as a personal computer or a work station, to execute an output program (an ultrasonic imaging program) prepared beforehand. The ultrasonic imaging method can be distributed via a network such as the Internet. Furthermore, the ultrasonic imaging method can be recorded in a computer readable, non-transitory recording medium such as a hard disk, a flexible disc (FD), a compact disc read only memory (CD-ROM), a magneto-optical disk (MO), or a digital versatile disc (DVD) to be read and executed from the recording medium by a computer.

Furthermore, in the embodiments and the modification examples described above, the term "real-time" means that, each time data to be processed is generated, processing is immediately executed. For example, the processing of displaying an image in a real-time manner is not limited to a case in which the time when a subject is photographed and the time when an image is displayed fully coincide with each other. The processing of displaying an image in a real-time manner represents an idea including a case in which an image is displayed in a slightly delayed manner due to a period of time required for processing such as image processing.

According to at least one of the embodiments described above, it is possible to reduce overlooked diseases.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic device, comprising:
processing circuitry configured to
execute ultrasonic scanning of a subject to generate ultrasonic image data;
estimate a health state of the subject based on a measurement value measured using the generated ultrasonic image data;
determine, based on the estimated health state of the subject, an additional examination used to diagnose the health state among additional ultrasound examinations executable in various types of ultrasonic imaging modes, each being used in accordance with a corresponding purpose of an examination using the ultrasonic diagnostic device; and
output information indicative of the estimated health state and the determined additional examination.

2. The ultrasonic diagnostic device according to claim 1, wherein the processing circuitry is further configured to determine the additional examination based on a current imaging mode used to capture the ultrasonic image data.

3. The ultrasonic diagnostic device according to claim 1, wherein the processing circuitry is further configured to
determine a degree of priority for each of the additional ultrasound examinations, and
output information indicative of the degrees of priority for the additional ultrasound examinations.

4. The ultrasonic diagnostic device according to claim 3, wherein the processing circuitry is further configured to determine the degree of priority for each additional ultrasound examination of the additional ultrasound examinations based on whether the additional ultrasound examination is an additional examination that is executed under an imaging mode identical to a current imaging mode.

5. The ultrasonic diagnostic device according to claim 3, wherein the processing circuitry is further configured to determine the degree of priority for each of the additional ultrasound examinations based on whether the additional ultrasound examination is an additional examination that is executed under a B-mode.

6. The ultrasonic diagnostic device according to claim 1, wherein the processing circuitry is further configured to perform, when an imaging mode for the determined additional examination and a current imaging mode differ from each other, switching of the imaging mode.

7. The ultrasonic diagnostic device according to claim 1, wherein the processing circuitry is further configured to estimate the health state based on non-image information that differs from the ultrasonic image data.

8. The ultrasonic diagnostic device of claim 1, wherein the processing circuitry is further configured to execute the determined additional examination to generate additional ultrasonic image data.

9. An output method for ultrasonic imaging, the method comprising:
executing by processing circuitry of an ultrasonic diagnostic device, ultrasonic scanning of a subject to generate ultrasonic image data;
estimating, by the processing circuitry, a health state of the subject based on a measurement value measured using the ultrasonic image data;
determining, by the processing circuitry, an additional examination used to diagnose the health state among additional ultrasound examinations executable in various types of ultrasonic imaging modes, each being used in accordance with a corresponding purpose of an examination using the ultrasonic diagnostic device, based on the estimated health state; and
outputting, by the processing circuitry, information indicative of the estimated health state and the determined additional examination.

10. A computer program product having a non-transitory computer-readable recording medium including a plurality of instructions executable by processing circuitry of an ultrasonic diagnostic device, wherein the instructions, when executed by the processing circuitry, cause the processing circuitry to perform an output method for ultrasonic imaging, the method comprising:
executing ultrasonic scanning of a subject to generate ultrasonic image data:
estimating a health state of the subject based on a measurement value measured using the ultrasonic image data,
determining based on the estimated health state, an additional examination used to diagnose the health state among additional ultrasound examinations executable in various types of ultrasonic imaging modes, each being used in accordance with a corresponding purpose of an examination using the ultrasonic diagnostic device, and outputting information indicative of the estimated health state and the determined additional examination.

\* \* \* \* \*